United States Patent [19]

Kitakaze

[11] Patent Number: 5,700,803
[45] Date of Patent: Dec. 23, 1997

[54] METHOD FOR REDUCING INFARCT SIZE IN SUBJECTS AFFLICTED WITH ISCHEMIC HEART DISEASE

[75] Inventor: Masafumi Kitakaze, Osaka, Japan

[73] Assignee: Otsuka Pharmaceutical Co., Ltd., Tokyo, Japan

[21] Appl. No.: 570,767

[22] Filed: Dec. 12, 1995

[51] Int. Cl.$^6$ .................................................. A61K 31/495
[52] U.S. Cl. ............................................ 514/254; 514/255
[58] Field of Search ................................ 514/255, 254

[56] References Cited

U.S. PATENT DOCUMENTS 5,504,093  4/1996  Gelfand ................................. 514/314

FOREIGN PATENT DOCUMENTS 0552373  7/1993  European Pat. Off. .

OTHER PUBLICATIONS

Ver Donck K. Pharm. World Sci. 16 (2), pp. 69–76, 1994.
Forker et al, *J. Clin. Pharmacol.*, 36;973–984 (1996).
Sasayama et al, *Heart and Vessels*, 2:23–28 (1986).
Feldman et al, *Am. J. Cardiol*, 68:1203–1210 (1991).

"Effects of the Oral Cardiotonic Piperanometozine Upon Ischemic Myocardium", *Shinzo (Cardiology)*, 20(6):670–678 (1988) (in Japanese and English Translations).

"Effects of the Cardiovascular Agonist OPC–8212 Against Ischemic Heart Disease—Comparative Investigation with the β–Blocker Metoprolol", 36(11):1199–1203 (1988) (in Japanese and English Translations).

Maruyama et al, "Effects of OPC–8212, a New Positive Inotropic Agent, and Dobutamine on Left Ventricular Global and Ischemic Regional Functions and Coronary Hemodyamics Under Coronary Artery Stenosis", *J. Cardiovasc. Pharmacol.*, 8(1):161–169 (1986).

Takeya et al, "Positive Inotropic Effect of 3,4–Dihydro–6–[4–(3,4–Dimethoxybenzoyl)–1–Piperazinyl]–2(1H)–Quinolinone (OPC–8212) and Mechanism of Action in Guinea Pig Ventricular Myocardium", *Arzneim.–Forsch./Drug Res.*, 34(1), Nr.3a:364–370 (1984).

Primary Examiner—C. Warren Ivy
Assistant Examiner—Evelyn Huang
Attorney, Agent, or Firm—Sughrue, Mion, Zinn, Macpeak & Seas, PLLC

[57] ABSTRACT

A method for reducing infarct size in a subject afflicted with ischemic heart disease, is disclosed, wherein said method uses, as the active agent, a carbostyril derivative.

2 Claims, No Drawings

METHOD FOR REDUCING INFARCT SIZE IN SUBJECTS AFFLICTED WITH ISCHEMIC HEART DISEASE

FIELD OF THE INVENTION

The present invention relates to a method for reducing infarct size in a subject afflicted with ischemic heart disease, wherein said method uses, as the active agent, a carbostyril derivative.

BACKGROUND OF THE INVENTION

I. Carbostyrils

Carbostyril derivatives represented by the following general formula (1), and salts thereof:

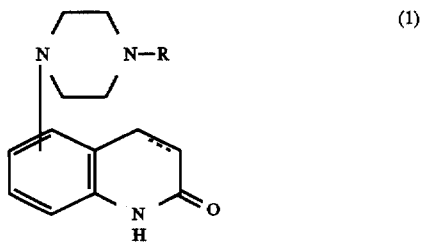

wherein R is a benzoyl group which may optionally have lower alkoxy groups on the phenyl ring as substituents and the carbon-carbon bond in the 3 and 4 positions of the carbostyril skeleton is a single bond or double bond, are well-known in the art (U.S. Pat. No. 4,415,572, which is incorporated by reference herein in its entirety).

These carbostyrils have been found to be an oral inotropic agent that augments myocardial contractility in model systems, with little effect on the heart rate or myocardial oxygen consumption (Feldman et al, N. Engl. J. Med., 329:149–155 (1993)), and are useful for treatment of patients with congestive heart failure (U.S. Pat. No. 4,415, 572; and Hori et al, Jpn. Circ. J., 50:659–666 (1986)). Several studies have demonstrated that the above carbostyrils improve hemodynamic indexes, and exercise capacity in congestive heart failure patients (Inoue et al, Heart Vessels, 2:166–171 (1986); Sasayama et al, Heart Vessels, 2:23–28 (1986); and Feldman et al, Am. Heart J., 116:771–777 (1988)). In addition, multi-center randomized placebo-controlled trials both in Japan and in the United States have demonstrated that these carbostyrils improved quality of life and reduced the risk of death in patients with congestive heart failure (OPC-8212 Multicenter Research Group, Cardiovasc. Drugs Ther., 4:419–425 (1990); Feldman et al, Am. J. Cardiol., 68:1203–1210 (1991); and Feldman et al, N. Engl. J. Med., 329:149–155 (1993)).

The mechanisms of action associated with the inotropic properties of these carbostyrils include a decrease in potassium current (Iijima et al, J. Pharmacol. Exp. Ther., 240:657–662 (1987)), a mild inhibition of phosphodiesterase, and an increase in the inward calcium current (Yatani et al, J. Cardiovasc. Pharmacol., 13:812–819 (1989); and Taira et al, Arzneimittelforschung, 34:347–355 (1984)). However, the dose of the carbostyrils which was most effective in reducing mortality (60 mg daily) showed no or little hemodynamic effect, implying that the drug may reduce mortality through another mechanism, rather than its positive inotropic effect (Feldman et al, N. Engl. J. Med., 329:149–155 (1993); and Packer, N. Engl. J. Med., 329:201–202 (1993)).

The above carbostyrils are also known to inhibit the production of various cytokines, including TNF-α and IL-6, by lipopolysaccharide-stimulated peripheral blood mononuclear cells (PBMC) in a dose-dependent manner (Maruyama et al, Biochem. Biophys. Res. Commu., 195:1264–1271 (1993); and Matsumori et al, Circul., 89:955–958 (1994)).

Moreover, they can induce a reversible neutropenia associated with a decrease in CFU-C (Feldman et al, Am. Heart J., 116:771–777 (1988); OPC-8212 Multicenter Research Group, Cardiovasc. Drugs, Ther., 4:419–425 (1990); Feldman et al, Am. J. Cardiol., 68:1203–1210 (1991); and Feldman et al, N. Engl. J. Med., 329:149–155 (1993)).

Additionally, the above carbostyrils have been found to be useful in regulating apoptosis (programmed cell death), and in the treatment of cancer, inhibition of tumor metastasis and inhibition of RNA virus replication (U.S. patent application Ser. No. 07/989,028, filed Apr. 30, 1993, which corresponds to European Patent Publication 0552373, each of which is incorporated by reference herein in their entirety; Nakai et al, Jpn. J. Cancer Res., Abstract, and Proc. Jpn. Cancer Assoc., page 581 (1993); and Maruyama et al, Biochem. Biophys. Res. Comm., 195:1264–1271 (1993)).

The above carbostyrils are also useful for inhibiting DNA virus replication and provide a synergistic effect, when used together with an anti-RNA virus compound, in inhibiting RNA virus replication (U.S. patent application Ser. No. 08/283,707, Aug. 1, 1994; and PCT/US95/09141, filed Jul. 28, 1995).

Moreover, the above carbostyrils have been found to be useful in inhibiting nucleoside and nucleobase transport, e.g., adenosine, in mammalian cells in a dose-dependent manner, and in augmenting phosphorylation of nucleoside analogues, particularly, AZT (U.S. patent application Ser. No. 08/283,707, Aug. 1, 1994; and PCT/US95/09141, filed Jul. 28, 1995). On the other hand, only high concentrations (outside of the therapeutic range) of dipyridamole (10–100 µM), another nucleoside transport inhibitor, inhibit adenosine transport (Scholtissek et al, Biochem. Biophys. Acta, 158:435–447 (1968); and Plagemann et al, J. Membr. Biol., 81:255–262 (1984)).

Dipyridamole is proposed to cause a localized increase in adenosine concentration through its inhibition of adenosine transport into cells (Plagemann et al, Biochem. Biophys. Acta, 947:405–443 (1988)). Adenosine is known to induce an increase in cAMP in myocardial cells either through activation of adenylate cyclase or through inhibition of phosphodiesterase (Fox et al, Ann. Rev. Biochem., 47:655–686 (1978); and Takeya et al, Drug Res., 34:364–370 (1984)), dilation of coronary arteries (Fox et al, Ann. Rev. Biochem., 47:655–686 (1978)), an increase in cerebral blood flow (Heistad et al, Am. J. Physiol., 240:775–780 (1981)), a decrease in TNF-α production (Parmely et al, J. Immunol., 151:389–396 (1993)), and a decrease in platelet aggregation (Dawicki et al, Biochem. Pharmacol., 34:3965–3972 (1985)), through its binding to specific adenosine receptors on cell surface membranes.

Inhibition of adenosine transport caused by carbostyrils is believed to provide the link with another novel aspect of their action. That is, the above carbostyrils might increase blood concentrations of adenosine by inhibiting adenosine transport, thus explaining some of the therapeutic benefit of vesnarinone in congestive heart disease (Feldman et al, N. Engl. J. Med., 329:149–155 (1993); and Packer, N. Engl. Med., 329:201–202 (1993)) or in the reduction of TFN-α production (Maruyama et al, Biochem. Biophys. Res. Comm., 195:1264–1271 (1993); and Matsumori et al, Circul., 89:955–958 (1994)).

II. Ischemic Heart Disease

Although ventricular dysfunction occurs in patients with chronic heart failure and ischemic heart disease, the pathophysiology of these two cardiac diseases is quite difference. That is, in chronic heart failure, the responsiveness of the myofilaments to $Ca^{2+}$ is reduced due to impairment of sympathetic nerve regulation, as well as to impairment of the renin-angiotensin and cytokine systems. On the other hand, in ischemic heart disease, cellular anaerobic metabolism produces reversible and irreversible cellular damage, leading to ventricular dysfunction. Anaerobic myocardial metabolism is mainly attributable to impairment of regulation of coronary blood flow.

Carbostyrils have been found to increase coronary blood flow in ischemic regions, which is postulated to be due to increased aortic blood pressure and coronary dilation action (Maruyama et al, *J. Cardiovasc. Pharmacol.*, 8:161–169 (1986)). However, increases in aortic blood pressure can cause increased coronary blood flow, and may result in increased oxygen demand. This may blunt the beneficial effects of coronary vasodilation.

However, carbostyrils have also been found to give rise to improvements in exercise-induced ischemia without change in heart rate or systolic blood pressure, and to block the progression of ischemia (Kinoshita et al, *Respir. Circ.*, 36:1199–1203 (1988)). Although increases in coronary blood flow may imply attenuation of myocardial ischemia, since the extent of myocardial ischemia is blood flow-dependent, infarct size is not determined by coronary vasodilatory capacity. This is because the coronary artery is completely occluded during myocardial ischemia. The progression of myocardial infarction is attributable to the speed of ATP depletion, and the extent of collateral flow during ischemia, and to platelet and neutrophil activation, $Ca^{+2}$ and catecholamine overload, and oxygen-derived free radical generation. Thus, attenuation of myocardial ischemia due to coronary vasodilation does not necessarily imply limitation of infarct size.

Carbostyrils have also been shown to improve ST depression during exercise in patients with coronary artery disease (Kinoshita et al, supra). The ST-T level in electrocardiogram changes due to the intra- and extracellular balances in $Ca^{2+}$, $K^+$, H and $Na^+$, rotation of the heart, ventricular wall motion, and the presence of ischemia (Noble et al *Cardiovasc. Res.*, 12:13–17 (1978)). Thus, there is no suggestion therein that carbostyrils can improve myocardial ischemia. Even if myocardial function of the ischemic area is improved due to coronary vasodilation caused by carbostyrils, attenuation of ischemia does not indicate reduction in infarct size. This is because of the multiple coronary blood flow-independent pathogenesis of myocardial necrosis.

In the present invention, it has been unexpectedly discovered that carbostyrils attenuate myocardial ischemia and reduce infarct size. This is surprising since the carbostyrils are classified as positive inotropic agents, and positive inotropic agents are known to expand ischemic damage (Blaiklogk et al, *J. Mol. Cell. Cardiol.*, 10:499–509 (1987)).

SUMMARY OF THE INVENTION

An object of the present invention is to provide a method for reducing infarct size in a subject afflicted with ischemic heart disease.

These and other objects of the present invention, which will be apparent from the detailed description of the invention provided hereinafter, have been met by the use of a carbostyril derivative represented by the following general formula (1), and salts thereof:

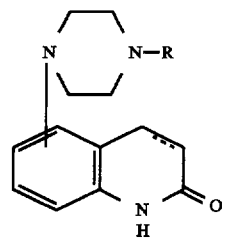

wherein R is a benzoyl group which may optionally have lower alkoxy groups on the phenyl ring as substituents and the carbon-carbon bond in the 3 and 4 positions of the carbostyril skeleton is a single bond or double bond.

DETAILED DESCRIPTION OF THE INVENTION

In general formula (1), the benzoyl group which may have lower alkoxy groups and substituents on the phenyl ring, includes benzoyl groups having 1 to 3 straight-chain or branched $C_{1-6}$ alkoxy groups substituting the phenyl ring, such as benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isobutoxybenzoyl, 4-hexloxybenzoyl, 3,4-dimethoxybenzoyl, 3,4-diethoxybenzoyl, 3,4,5-trimethoxybenzoyl, 2,5-dimethoxybenzoyl, and so on.

Of the active ingredient compound (1) according to the invention, 3,4-dihydro-6-[4-(3,4-dimethoxybenzoyl)-1-piperazinyl]-2(1H)-quinoline, i.e., vesnarinone, is most preferable.

The above carbostyrils will readily form a salt with a conventional acid. As such acids, there may be mentioned inorganic acids, such as sulfuric acid, nitric acid, hydrochloric acid and hydrobromic acid; and organic acids, such as acetic acid, p-toluenesulfonic acid, ethanesulfonic acid, oxalic acid, maleic acid, fumaric acid, citric acid, succinic acid and benzoic acid. These salts can also be used as the active ingredient in the present invention, just as can the free compound of general formula (1).

The compounds of general formula (1) and salts thereof, can be generally formulated into the per se conventional pharmaceutical preparations. Such preparations are prepared using conventional fillers, extenders, binding agents, moistening agents, disintegrating agents, surfactants, lubricants, and the like diluents or excipient. These pharmaceutical preparations may have various dosage forms selected according to the purposes of therapy, and typical examples thereof are tablets, pills, powders, solutions, suspensions, emulsions, granules, capsules, suppositories, injections (solutions, suspensions, etc.), and ophthalmic solutions.

For the manufacture of tablets, a wide variety of carriers so far well-known in this field can be used. Thus, use can be made of, for example, vehicles or excipient, such as lactose, sucrose, sodium chloride, glucose, urea, starch, calcium carbonate, kaolin, crystalline cellulose and silicic acid; binding agents, such as water, ethanol, propanol, simple syrup, glucose solution, starch solution, gelatin solution, carboxymethylcellulose, shellac, methylcellulose, potassium phosphate and polyvinylpyrrolidone; disintegrating agents, such as dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch and lactose; disintegration inhibitors, such as sucrose, stearin, cacao butter and hydrogenated oils; absorption promoters, such as quaternary ammonium bases and sodium lauryl sulfate; wetting agents or humectants, such as glycerol and starch; adsorbents, such as starch, lactose, kaolin, bentonite and colloidal silica; and lubricants, such as refined talc, stearic acid salts, powdered boric acid and polyethylene glycol. When necessary, the tablets may further be provided with a conventional coating to give, for example, sugar-coated tablets, gelatin-coated tablets, enteric-coated tablets, film-coated tablets, or double-coated or multilayer tablets.

For the manufacture of pills, a wide variety of carriers well-known in the art can be used. Examples are vehicles or excipients, such as glucose, lactose, starch, cacao butter, hardened vegetable oils, kaolin and talc; binding agents, such as powdered gum arabic, powdered tragacanth gum, gelatin and ethanol; and disintegrating agents, such as laminaran and agar.

For the manufacture of suppositories, a wide variety of known carriers can be used. As examples, there may be mentioned polyethylene glycol, cacao butter, higher alcohols, higher alcohol esters, gelatin and semisynthetic glycerides.

In preparing injections, the solutions or suspensions are preferably sterilized and are preferably isotonic with blood and, for preparing such dosage forms, all of the diluents in conventional use in the field can be employed. Thus, for example, water, ethyl alcohol, propylene glycol, ethoxylated isostearyl alcohol, polyoxylated isostearyl alcohol and polyoxyethylene sorbitan fatty acid esters may be mentioned. In this case, the pharmaceutical preparations may contain sodium chloride, glucose or glycerol in an amount sufficient to give isotonic solutions. It is possible to add conventional solubilizing agents, buffers, soothing agents or local anesthetics, etc.

Furthermore, when necessary, the pharmaceutical preparations may contain coloring matters, preservatives, perfumes, flavoring agents, sweetening agents and the like, as well as other drugs.

The proportion of the active ingredient compound in these pharmaceutical preparations for use in the present invention is not critical, and may suitably be selected over a wide range. Generally, however, the proportion is recommendably selected within the range of about 1.0 to about 70% by weight, preferably about 1.0 to about 30% by weight.

The route of administration of the pharmaceutical preparations of the present invention is not critical, either, but is selected according to the dosage form, the patient's age, sex and other factors, and the severity of the disease to be treated. Thus, for instance, when they are provided in the form of tablets, pills, solutions, suspensions, emulsions, granules or capsules, the preparations are administered orally. Injectable solutions are administered intravenously, either alone or in admixture with conventional fluids for parental infusion containing glucose, amino acids and so on. Where necessary, these solutions may also be administered as is by the intramuscular, intradermal, subcutaneous or intraperitoneal route. Suppositories are administered rectally, ophthalmic solutions are drop lotions for the eyes.

While the dosage of the above pharmaceutical preparations is dependent on the method of administration, the patient's age, sex and other background factors, severity of the disease and so on, it is generally recommended to administer about 0.5 to 30 mg, as the active ingredient, viz. compound (1), per kilogram body weight per day. The amount of the active ingredient to be contained in each dosage unit is about 10 to 1000 mg.

Dosage Form Example 1

| | |
|---|---|
| 3,4-dihydro-6-[4-(3,4-dimethyoxybenzoyl)-1-piperazinyl]-2(1H)-quinoline | 150 g |
| Avicel | 40 g |
| (trademark, Asahi Chemical Industry, Co., Ltd.) | |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Methanol | 40 g |

The above active ingredient, Avicel, corn starch and magnesium stearate are mixed and ground together, and the resulting mixture is compression-molded with a dragee R10 mm punch. The tablets thus obtained are coated with a film coating composition consisting of hydroxypropyl methylcellulose, polyethylene glycol 6000, castor oil and methanol to give film-coated tablets.

Dosage Form Example 2

| | |
|---|---|
| 3,4-dihydro-6-[4-(3,4-dimethoxybenzoyl)-1-piperazinyl]-2(1H)-quinoline | 150 g |
| Citric acid | 1 g |
| Lactose | 33.5 g |
| Dicalcium phosphate | 70 g |
| Pluronic F-68 | 30 g |
| Sodium lauryl sulfate | 15 g |
| Polyvinylpyrrolidone | 15 g |
| Polyethylene glycol (Carbowax 1500) | 4.5 g |
| Polyethylene glycol (Carbowax 6000) | 45 g |
| Corn starch | 30 g |
| Dry sodium lauryl sulfate | 3 g |
| Dry magnesium stearate | 3 g |
| Ethanol | q.s. |

The above active ingredient, citric acid, lactose, dicalcium phosphate, pluronic F-68 and sodium lauryl sulfate are admixed.

After size selection using a No. 60 screen, the mixture is granulated by the wet process using an alcoholic solution containing polyvinylpyrrolidone, Carbowax 1500 and Carbowax 6000. When necessary, alcohol is added to make the powder into a paste-like mass. Then, corn starch is added, and the blending is continued until uniform granules are formed. The mixture is then passed through a No. 10 screen, placed in a tray and dried in an oven maintained at 100° C. for 12 to 14 hrs. The dried granules are sieved through a No. 16 screen, then dry sodium lauryl sulfate and dry magnesium stearate are added and, after blending, the mixture is compressed to a desired size and shape using a tableting machine.

The above cores are treated with a varnish and dusted with talc for preventing absorption of moisture, and then provided with an undercoat layer. Varnish coating is repeated as many times as sufficient for internal use. The tablets are rendered completely round and smooth by application of a further undercoat layer and a smooth coating. Color coating is conducted until a desired coloring is obtained. After drying, the coated tablets are polished to give uniformly polished tablets.

The following examples are provided for illustrative purposes only, and are in no way intended to limit the scope of the present invention.

EXAMPLE 1

Effects of Vesnarinone on Adenosine Concentration in Blood

Mongrel dogs weighing 15–20 kg were anesthetized by intravenous administration of 30 mg/kg of pentobarbital sodium. Then, their trachea were incubated, and the animals were ventilated with room air mixed with oxygen. Next, their chests were opened through the left fifth intercostal space, and their hearts were suspended in a pericardial cradle. The left anterior descending coronary artery (LAD) of each animal was cannulated and perfused with blood via the left carotid artery through an extracorporeal bypass tube.

Coronary perfusion pressure (CPP) was monitored at the tip of the coronary arterial cannula.

Coronary blood flow (CBF) of the perfused area was measured with an electromagnetic flow probe attached at the bypass tube.

A small, short collecting tube (1.0 mm in diameter and 7.0 cm in length) was inserted into a small coronary vein near the center of the perfused area to sample coronary blood. The drained venous blood was collected in a reservoir placed at the level of the left atrium, and was returned to the jugular vein.

The concentration of lactate in the blood was assessed by an enzymatic assay (Bergmeyer, *Methods of Enzymatic Analysis*, Academic Press, New York (1963), pages 266–270), and the lactate extraction ratio, calculated as the coronary arteriovenous difference in lactate concentration multiplied by 100 and divided by the arterial lactate concentration, was calculated.

To monitor the conditions of the dogs, their blood pressure was measured using a AP-641G blood pressure amplifier (Nihon Koden), and their systemic blood was sampled for blood gas analysis, including pH and $PO_2$, using an ABL300 gas analyzer (Radiometer, Copenhagen).

With the use of an occluder that produces a quantitative stenosis of the perfusion tube, the extent of stenosis to reduce CBF to 33% and 60% of the control flow was defined. After this procedure, attachment of this occluder produced a stable hypoperfusion for 10 min, and measurements of all variables were performed 20 min after the onset of the coronary arterial clamp.

After the above measurements, vesnarinone's vehicle (1.0% (v/v) dimethylsulfoxide, DMSO) was infused into the LAD for 5 min, and all of the above hemodynamic and metabolic parameters were measured. Thus, using an infusion pump, 0.54 mg/ml of vesnarinone was infused into the LAD, at an infusion rate of 0.2–0.5 ml/min, so as to achieve 15 µg/ml. All of the above hemodynamic and metabolic parameters were again measured at 5 and 10 min after the infusion.

The blood concentration of adenosine was measured by drawing 1.0 ml of blood into a syringe containing 0.5 ml of 0.02% (w/v) dipyridamole and 100 µl of a 0.1 mg/ml solution of 2'-deoxycoformycin in 500 mM EDTA to block both the uptake of adenosine by red blood cells and the degradation of adenosine. After centrifugation (3000×g), the supernatant was collected and its adenosine concentration was measured by radioimmunoassay. Specifically, the adenosine in 100 µl of plasma was succinylated with 100 µl of dioxane containing 40 mg of succinic acid anhydride and 0.4 mg of triethylamine. After incubation for 20 min at 4° C., the mixture was diluted with 100 µl of diluted anti-adenosine serum (Yamasa-Shyoyu, Chiba, Japan) and 100 µl of 0.5 pmol adenosine 2',3'-O-disuccinyl-3[$^{125}$I]iodotyrosine methyl ester. The mixture was kept in a cold water bath (4° C.) for 18 hr, and 500 µl of the second antibody solution (goat anti-rabbit IgG) (Yamasa-Shyoyu, Chiba, Japan) anti-serum was added. After incubation at 4° C. for 60 min, the unreacted material was removed by centrifugation at 3000 rpm (2,500×g) at 4° C. for 20 min. The radioactivity remaining in the tube was counted using a gamma counter. Adenosine degradation during this blood sampling procedure has been reported to be negligible (Yamane, *J. Immunol.*, 12:501–519 (1991); Sato et al, *Ann. Biochem.*, 121:409–420 (1982); Hori et al, *Am. J. Physiol.*, 250:14509–14518 (1986); and Kitakaze et al, *Circ. Res.*, 60:631–630 (1987)). This method, using the specific antibody, was sensitive enough to detect as low as 5.0 pmol/ml of adenosine. The coefficient of variance of intraassay and interassay was observed to be 1.3–3.1% and 4.1–4.9%, respectively. This sensitive radioimmunoassay method for adenosine measurement does not need to remove protein, which is usually performed in the HPLC measurements for adenosine. The results are shown in Table 1 below for a representative dog.

TABLE 1

| Time (min) | Coronary Blood Flow (ml/min) | Lactate Concentration (mg/dl) | Adenosine Concentration (pmol/ml) |
|---|---|---|---|
| 0 Onset of Hypoperfusion | 21 | 16.4 | 9.3 |
| 20 DMSO | 12 | 17.1 | 15.0 |
| 25 Vesnarinone | 12 | 17.0 | 14.0 |
| 30 | 12 | 16.7 | 23.8 |
| 35 | 12 | 16.7 | 24.2 |

As shown in Table 1 above, when CPP was decreased from 96 to 53 mmHg so that CBF decreased to 60% of the baseline flow, the concentrations of lactate and adenosine in coronary venous blood were increased. On the other hand, the concentrations of lactate (19.5 mg/dl) and adenosine (7.2 pmol/ml) in coronary arterial blood were not changed due to the reduction of CPP throughout the study. Thereafter, CBF was kept constant. DMSO infusion during coronary hypoperfusion did not result in any change in CPP or the concentration of lactate and adenosine in coronary venous blood.

However, as shown in Table 1 above, during infusion of vesnarinone, adenosine concentration in coronary venous blood was increased despite unchanged CBF and lactate concentrations in coronary venous blood. Although, CPP was decreased (from 53 to 51 mmHg) due to the coronary vasodilator effects of adenosine. These results indicate that vesnarinone potentiates the release of adenosine in the ischemic myocardium.

EXAMPLE 2

Effects of Vesnarinone on Coronary Blood Flow

With an occluder attached at the extracorporeal bypass tube of the above-discussed dogs, CPP was reduced so that CBF decreased to 60% of the control CBF. After the low CPP was determined, the occluder was adjusted to keep CPP constant at the low level. All of the above hemodynamic parameters, and coronary arterial and venous blood for the metabolic parameters were measured 10 min after the onset of hypoperfusion. After these measurements, vesnarinone's vehicle (1.0% (v/v) DMSO) was infused into the LAD, and all of the above hemodynamic and metabolic parameters were measured at 5 min after the infusion. Next, using an infusion pump, 0.54 mg/ml of vesnarinone was infused into the LAD, at an infusion rate of 0.2–0.5 ml/min, so as to achieve 15 μg/ml. All of the hemodynamic and metabolic parameters were again measured at 5 min and 10 min after the infusion. The results are shown in Table 2 below for a representative dog.

TABLE 2

| Time (min) | Coronary Blood Flow (ml/min) | Lactate Concentration (mg/dl) | |
|---|---|---|---|
| | | Coronary Venous Blood | Coronary Arterial Blood |
| 0 Onset of Hypoperfusion | 20 | 10.6 | 13.1 |
| 10 DMSO | 12 | 13.8 | 13.1 |
| 15 Vesnarinone | 12 | 14.0 | 12.9 |
| 20 | 13 | 11.5 | 13.2 |
| 25 | 14 | 10.8 | 13.2 |

As shown in Table 2 above, when CPP was reduced from 93 to 59 mmHg so that CBF decreased to 60% of the baseline flow, lactate concentration in coronary venous blood was increased, but lactate concentration was unchanged in coronary arterial blood. Thereafter, CPP was kept constant. DMSO did not change CBF or the lactate concentration of coronary arterial blood. However, vesnarinone increased CBF, and decreased the lactate concentration of coronary venous blood. These results demonstrate that vesnarinone can increase CBF, i.e., coronary vasodilation, in ischemic myocardium, and decreases the severity of ischemia.

EXAMPLE 3

Effects of Vesnarinone on Infarct Size

Perfusion with adenosine can markedly limit infarct size (Olafsson, *Circ.*, 76:1135–1145 (1987)), and as shown in Example 1 above, vesnarinone can increase adenosine blood concentration. Thus, tests were carried out to determine if vesnarinone also causes reduction in infract size.

More specifically, the LAD of the above-described dogs was isolated and a strip of moistened umbilical tape was passed around the vessels for the occlusion, which was accomplished by snaring it into a small plastic tube. The regional blood flow in the left atrium was catheterized for microsphere injection.

Regional CBF was determined by the microsphere technique, which uses non-radioactive microspheres (Sekisui Plastic Co., Ltd., Tokyo, Japan) made of inert plastic labeled with different stable heavy elements, as described by Mori et al, *Am. J. Physiol.*, 263:141946–141957 (1992).

More specifically, microspheres labeled with Br or Zr, and having a mean diameter of 15 μm were used. The specific gravity was 1.34 for Br and 1.36 for Zr. The microspheres were suspended in isotonic saline with 0.01% (v/v) Tween 80 to prevent aggregation. The microspheres were ultrasonicated for 5 min, followed by 5 min of vortexing immediately before injection. 1.0 ml of the microsphere suspension (2–4×10⁶ spheres) was injected into the left atrium followed by several warm (37° C.) 5.0 ml saline flushes. The microspheres were administered at 80 min after the onset of coronary occlusion. Just before microsphere administration, a reference blood flow sample was withdrawn from the femoral artery at a constant rate of 8.0 ml/min for 2 min. The X-ray fluorescence of the stable heavy elements was measured by a PW 1480 wavelength dispersive spectrometer (Phillips Co., Ltd., Almelo, The Netherlands). When the microspheres are irradiated by the primary X-ray beam, the electrons fall back to a lower orbit and emit measurable energy with a characteristic X-ray fluorescence energy level for each element. Therefore, it is possible to qualify the X-ray fluorescence of several species of labeled microspheres in a single mixture. Regional CBF was calculated according to the formula: time flow=(tissue counts)× (reference flow)/(reference counts), and was expressed in ml/min/g net weight.

As a control, after 20 min of hemodynamic stabilization, the LAD was occluded for 90 min and reperfused for 6 hr. Using an infusion pump, 0.90 mg/ml of vesnarinone was infused, at an infusion rate of 0.2–0.5 ml/min, 20 min before coronary occlusion, and during 1 hr of reperfusion after 90 min of coronary occlusion, so as to achieve 15 μg/ml.

After 6 hr of reperfusion, while the LAD was reoccluded and perfused with autologous blood, Evans blue dye was injected into a systemic vein to determine the anatomic risk area and the non-ischemic area in the hearts. The hearts were then removed immediately, and sliced into serial transverse sections 6–7 mm in width. The non-ischemic area was identified by blue stain, and the ischemic region was incubated at 37° C. for 20–30 min in 1.0% (w/v) 2,3,5-triphenyltetrazolium chloride (TTC; Sigma Chemical Co.) in 0.1M phosphate buffer (pH 7.4). TTC stained the non-infarcted myocardium to a brick-red color, indicating the presence of a formazin precipitate, which results from the reduction of TTC by dehydrogenase enzymes present in viable tissues. Infarct size was calculated as a percentage of the area at risk. The results are shown in the Table 3 below.

TABLE 3

| Treatment | Collateral Blood Flow (ml/min/100 g) | Risk Area (%) | Infarct Size (%) |
|---|---|---|---|
| DMSO (n = 5) | 7.2 ± 1.1 | 40.2 ± 2.3 | 43.5 ± 3.2 |
| Vesnarinone (n = 3) | 7.8 ± 1.3 | 41.1 ± 2.4 | 6.9 ± 3.9 |
| Dipyridamole (n = 5) | 6.9 ± 1.8 | 40.9 ± 3.8 | 35.0 ± 4.3 |
| Saline (n = 5) | 8.2 ± 2.0 | 41.8 ± 3.3 | 45.0 ± 4.2 |
| 8-SPT (n = 5) | 7.2 ± 1.7 | 38.9 ± 2.1 | 48.1 ± 4.5 |

As shown in the Table 3 above, although collateral blood flow during ischemia and the risk area in the DMSO and vesnarinone groups did not significantly vary, the infarct size was markedly reduced by administration of vesnarinone. This infarct size-limiting effect of vesnarinone was completely abolished 20 min after the vesnarinone-treated dogs were subjected to intracoronary infusion with 25 μg/kg/min of 8-sulfphenyltheophylline (8-SPT). 8-SPT is an adenosine receptor antagonist. Thus, the infarct-size limiting effect of vesnarinone may be mediated by increased adenosine release in an ischemic heart.

On the other hand, a significantly smaller decrease in infract size was observed when 10 μg/kg/min of the nucleoside transport inhibitor dipyridamole was infused, at an infusion rate of 0.2–0.4 ml/min, 20 min before coronary occlusion, and during 1 hr of reperfusion after 90 min of coronary occlusion.

The above results clearly demonstrate that the inotropic agent, vesnarinone, unexpectedly and markedly reduces infarct size.

Dipyridamole, which is known to increase adenosine release in ischemic heart, reduced infarct size less than vesnarinone. Although, dipyridamole is an adenosine nucleoside transport inhibitor as well as vesnarinone, these results appear to indicate that the action sites and tissue affinity of vesnarinone and dipyridamole are different, which may explain the unexpected differences of the potency on the infarct size-limiting effect.

While the invention has been described in detail, and with reference to specific embodiments thereof, it will be apparent to one of ordinary skill in the art that various changes and modifications can be made therein without departing from the spirit and scope thereof.

What is claimed:

1. A method for reducing infarct size in a subject afflicted with ischemic heart disease, comprising administering to said subject to a pharmaceutically effective amount of a carbostyril derivative represented by the following general formula (1), or a pharmaceutically acceptable salt thereof:

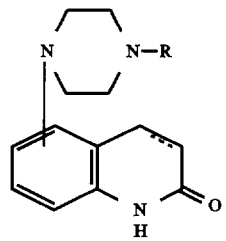
(1)

wherein R is a benzoyl group which may optionally have lower alkoxy groups on the phenyl ring as substituents and the carbon-carbon bond in the 3 and 4 positions of the carbostyril skeleton is a single bond or double bond.

2. The method of claim 1, wherein said carbostyril is 3,4-dihydro-6-[4-(3,4-dimethoxybenzoyl)-1-piperazinyl]-2(1H)-quinoline or a pharmaceutically acceptable salt thereof.

* * * * *